United States Patent [19]

Chang

[11] Patent Number: 5,283,344

[45] Date of Patent: Feb. 1, 1994

[54] COUPLING METHOD USING SELECTIVE AMINATION OF MALEIMIDE

[75] Inventor: Chi-Deu Chang, Green Oaks, Ill.

[73] Assignee: Abbott Laboratories, Abbott Park, Ill.

[21] Appl. No.: 29,265

[22] Filed: Mar. 10, 1993

[51] Int. Cl.$^5$ .......................................... C07D 207/40
[52] U.S. Cl. ...................................................... 548/546
[58] Field of Search ........................................ 548/546

[56] References Cited

U.S. PATENT DOCUMENTS 4,994,385  2/1991  Bieniarz et al. ...................... 548/522
5,204,366  4/1993  Lavanish et al. ..................... 548/546

OTHER PUBLICATIONS

Brewer, C. F. et al., (1967), "Evidence for Possible Nonspecific Reactions between N-Ethylmaleimide and Proteins", *Analytical Biochemistry* 18, 248–255.

Dell'Arciprete, L. D., et al., (1988), "A C Terminus Cysteine of Diphtheria Toxin B Chain involved in Immunotoxin Cell Penetration and Cytotoxicity", *Journal of Immunology* 140, No. 7, 2466–2471.

Kitagawa, T., et al., (1976), "Enzyme Coupled Immunoassay of Insulin Using a Novel Coupling Reagent", J. Biochem. 79, No. 1, 233–236.

Myers, D. E., et al., (1989), "The Effects of Aromatic and Aliphatic Maleimide Crosslinkers on Anti-CD5 Ricin Immunotoxins", *Journal of Immunolocial Methods*, 121, 129–142.

*Primary Examiner*—Mary C. Lee
*Assistant Examiner*—Joseph K. McKane
*Attorney, Agent, or Firm*—Lawrence S. Pope

[57] ABSTRACT

The instant invention is a method of coupling compounds comprising the steps of:
a) forming a maleimide derivative by reacting a maleimide containing compound having the formula:

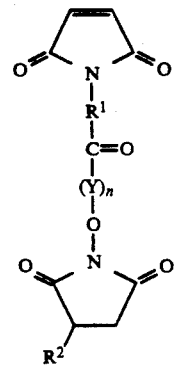

with an amine functional compound capable of displacing the N-hydroxysuccinimide group; and
b) reacting the derivitized maleimide of step (a) with a second amine functional compound.

8 Claims, No Drawings

COUPLING METHOD USING SELECTIVE AMINATION OF MALEIMIDE

TECHNICAL FIELD

Generally, the invention relates to a method of coupling compounds. More particularly, the invention relates to a method of heterobifunctionally coupling compounds using a compound containing a maleimido group.

BACKGROUND OF THE INVENTION

Heterobifunctional compounds having the general formula I (shown below) are well known as coupling agents that are useful for coupling chemical compounds.

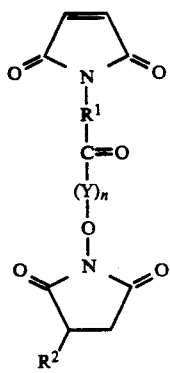

(I)

Some of the most commonly used coupling agents include: m-maleimidobenzoyl-N-hydroxysuccinimide ester (MBS), sulfosuccinimidyl 4-(p-maleimidophenyl)-butyrate (S-SMPB), m-maleimidobenzoylsulfosuccinimide ester (S-MBS) and N-γ-maleimidobutyryloxysuccinimide ester (GMBS).

Homobifunctional compounds have also been found useful as coupling agents. Examples of such compounds can be found in co-pending U.S. patent application Ser. No. 07/600,795 now abandoned which enjoys common ownership with the instant application.

Compounds having the general formula I have two reactive groups which serve as the basis for the utility of these compounds as coupling agents. The first reactive group is the N-hydroxysuccinimide group (NHS) or a water soluble analog thereof. At an alkaline pH, amino groups displace the NHS by nucleophilic attack of the ester. A reaction between a compound of formula I and an amine functional compound results in the acylation of the amino group of the amine functional polymer.

The second reactive group is the maleimide group which is reactive at the carbon-carbon double bond. In particular, at a neutral pH, the maleimide moiety is reactive at the carbon-carbon double bond with thiol groups, and such a reaction results in the formation of a thioether bond.

Presently, coupling two compounds using a compound of the formula I takes place in a stepwise manner and, generally, is performed in a two step process. The first step of the process takes place at a neutral or weakly alkaline pH and links an amine functional compound to a coupling agent as outlined above. The second step of the process takes place at a neutral pH and couples a thiol functional compound to the coupling agent in the manner previously stated. Hence, the amine functional compound and the thiol functional compound are coupled.

The method outlined above has been used to couple a variety of compounds. For example: Kitagawa et al., *J. Biochem.*, 79, 233-236 (1976). used MBS to couple insulin with β-D-galactosidase; Meyers, D. T. et al., *J. Immunol. Methods*, 121, 129-142 (1989), used MBS, S-MBS, GMBS and S-SMPB to couple an antibody to ricin (a toxin) to produce a immunotoxin (IT), and Dell-'Arciprete L. et al., *J. Immunol.*, 140, 2466-2471 (1988), used MBS to conjugate an antibody to diphtheria toxin to form an IT.

Although the aforementioned coupling method has been used successfully, it is limited in the types of compounds it can couple. More specifically, in order to successfully couple two compounds, the coupling method requires an amine functional compound and a thiol functional compound. If, for example, it were desired to couple two proteins (neither of which had a thiol group) it would be necessary to introduce a thiol group to one of the proteins in order to use the coupling method currently available. However, adding a thiol group to a compound may induce unwanted conformational changes to the compound and the removal of excess thiolating reagent is mandatory before the compound is coupled. Additionally, thiol groups are less stable at ambient conditions than, for instance, amine groups. Due to the necessity for a thiol group in the second step of the previously mentioned process, that process is limited in its application.

There is thus a need for a coupling process that does not require compound modification prior to coupling.

SUMMARY OF THE INVENTION

The present invention provides a method of coupling compounds comprising the steps of: a) forming a maleimide derivative by reacting a maleimide containing compound having the formula:

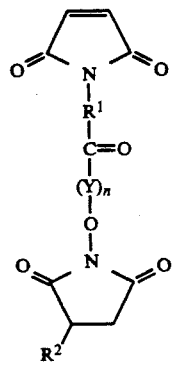

wherein $R^1$ is selected from the group consisting of $C_1$–$C_6$ alkyl, benzyl, $C_5$–$C_6$ cycloalkyl and combinations thereof;

Y is the residue of a substituted or unsubstituted amino acid;

n is from zero to ten; and $R^2$ is selected from the group consisting of, H, $KSO_3$, $LiSO_3$ and $NaSO_3$;

with an amine functional compound capable of reacting with the N-succinimide ester; and b) reacting the derivatized maleimide of step (a) with a second amine functional compound.

DETAILED DESCRIPTION OF THE INVENTION

Generally, the method of the instant invention can be carried out as shown below in Scheme 1.

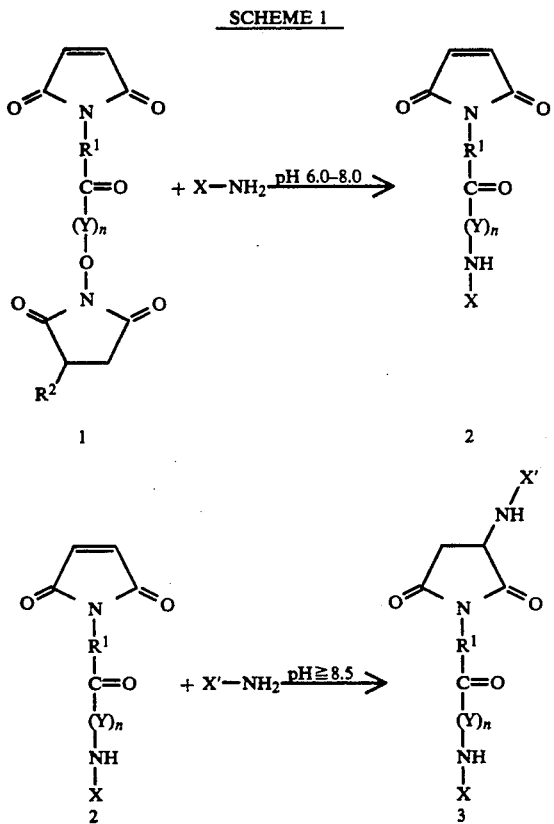

The method of the present invention can be carried out as shown in Scheme 1, wherein: $R^1$ and $R^2$ are defined as above; X is an amine functional compound; and X' is a second amine functional compound. It will be understood by those skilled in the art that the reactions of scheme 1 are carried out in buffers and under conditions suitable to the transformation being affected. The reagents and equipment necessary to carry out the invention are all commercially available and well known to those skilled in the art.

Scheme 1 shows, generally, the two step method of the present invention. As an initial matter, it is pointed out that while a primary amine is used to demonstrate both steps of the reaction the method is equally effective when compounds with secondary amines and/or —$CONHNH_2$ groups are randomly substituted for the primary amines shown in Scheme 1. The first step of the present invention is to react the compound of formula I with a compound having a primary amine, secondary amine or a —$CONHNH_2$ group. This reaction step takes place at a pH of between about 6.0 and 8.0 and the preferred pH range is between about 7.0 and 7.5. The second step of the present invention is to react the compound of formula 2 with a compound having a primary amine, secondary amine or a —$CONHNH_2$ group. This reaction step takes place at a pH of greater than or equal to 8.5, the preferred pH range is between about 8.5 and 9.0. The two step method yields a compound of the formula 3.

The first step of the procedure can be stoichiometrically executed so that substantially all of the reactants react to form a compound of the formula 2. The product of this reaction then can be used directly in the second step of the reaction. The second step of the reaction can also be stoichiometrically executed to yield a relatively pure compound of the formula 3.

Preferably, the first step of the coupling procedure is carried out with an excess of the amine functional compound. After the first step is completed, unreacted compounds can be removed from the compound of formula 2 using a variety of separatory techniques well known to those skilled in the art. Examples of these separatory techniques include solvent extraction, precipitation and gel chromotography. Similarly, it is also preferred, that the second step of the coupling procedure be carried out in an excess of amine functional compound and the separation of unreacted compounds from the compound of formula 3 can be accomplished as stated above. When excess amine functional compound is used for either step of the disclosed process, and the amine functional compound has a molecular weight of greater than approximately 1,000, it is particularly preferred that the coupled compound is purified from the excess reactants using size exclusion chromatography.

The term "amine functional compound" as used herein refers to compounds with a primary amine, secondary amine or a —$CONHNH_2$ group.

The term "substituted or unsubstituted amino acids" as used herein refers to naturally occurring and non-naturally occurring amino acids. Preferred non-naturally occurring amino acids are those which have from three to ten carbon atoms in a straight chain. Examples of coupling compounds which contain such amino acids can be found in U.S. Pat. No. 4,994,385 to Bieniarz et al. which is incorporated in its entirety herein by reference.

The method of the instant invention is a two step reaction that enables two amine functional compounds to be coupled without modifying the compounds prior to coupling. The second step of the coupling method herein disclosed allows an amine functional compound to react directly with the double bond of the maleimide group which is present on the coupling compound. The direct reaction of the amine functional compound with the double bond of the maleimide group is made possible by allowing the reaction to take place at a pH of greater than or equal to 8.5. Because the compounds do not require modification, for example by the addition of a thiol group, the method does not suffer from the problems previously mentioned.

Preferably, the first compound coupled to the compound of the formula I is an amine functional compound having a molecular weight between about 100 and 10,000. Compounds that are representative of those preferred for use in the first step of the instant invention are: haptens which include drugs, drug derivatives such as (4-aminomethyl)benzoylecgonine, 7,8-dihydromorphine-3-(2-aminothyl) ether and daunorubicin, signal generating groups such as 5-(aminomethyl)fluoroscein, and peptides such as sequence 190-209 of the human T-cell leukemia virus type-I envelope antigen; and toxins.

The second compound coupled to the compound of formula I is preferably an amine functional compound having a molecular weight above about 10,000. Compounds that are representative of those preferred for use in the second step of the instant invention are: hapten carriers which include large proteins such as bovine serum albumin, antibodies such as bovine gammaglobulin, and enzymes; and amine functional solid phases such as aminated beads, bead gels such as 6-aminohexyl Sepharose®, or amine derivatized microparticles.

Preferably, the method of the present invention may be used to create reagents that are employed in various assay systems which determine the presence, if any, of a substance in a test sample. For example, the method of the present invention can be used to couple an aminated solid phase, for instance aminated microparticles, with an antigen.

The method of the present invention also may be used to synthesize an indicator reagent comprising a monoclonal antibody, polyclonal antibody or a fragment thereof, which specifically binds to a substance being assayed, conjugated to a signal generating compound.

These reagents then can be used in an assay designed to determine the presence, if any, of a substance in a test sample. For example, the above mentioned coated solid phase is contacted with a test sample, which may contain, for example, antibodies to the coating antigen, to form a mixture. This mixture is incubated for a time and under conditions sufficient to form antigen/antibody complexes. Then, the indicator reagent, comprising an antibody, specific for the analyte antibody, conjugated to a signal generating compound, is contacted with the antigen/antibody complexes to form a second mixture. This second mixture is incubated for a time and under conditions sufficient to form antigen/antibody/antibody complexes. The presence of the particular substance in a test sample and captured on the solid phase, if any, is determined by detecting the measurable signal generated by the signal generating compound. The amount of substance present in the test sample is proportional to the signal generated.

In another embodiment of the method of the present invention, the method can be used to conjugate an antibody, antigen or fragments thereof to, for example, 6-aminohexyl sepharose®. The conjugated sepharose® may then be used to affinity purify a desired compound from cell cultures, biological tissues or biological fluids.

The following examples are provided to assist in illustrating the invention and not intended to limit the invention. All reagents and equipment necessary for carrying out the examples are commerically available and well known to those skilled in the art.

EXAMPLE 1

Maleimide Derivative of (4-aminomethyl)benzoylecgonine

A cocaine hapten (27.4 mg of (4-aminomethyl)benzoylecgonine hydrochloride) was dissolved in 1.15 ml of PH 7.5, 0.1M sodium phosphate buffer. Then the hapten solution was added to a mixing ice-chilled-solution which comprised 20.0 mg of succinimidyl 4-maleimidomethyl) cyclohexane-1-carboxylate in 0.5 ml of tetrahydrofuran to form a mixture. After the two solutions were combined the resultant solution was moved to room temperature and allowed to mix for three hours. Upon completion of the three hour mixihg period, a sample of the reaction mixture was taken and tested using thin layer chromatography (silica gel, developed with chloroform:methanol 3:1). The results of the thin layer chromotography showed a single uv spot at Rf=0.23. When a sample of unreacted cocaine hapten was tested using thin layer chromotography (silica gel, developed with chloroform:methanol 3:1), it showed up as a single uv spot at the origin. These results evidenced that nearly all of the cocaine hapten had reacted with the coupling agent.

EXAMPLE 2

Benzoylecgonine-BSA

An unpurified 1.4 ml aliquot of the maleimide derivatized (4-aminomethyl) benzoylecgonine (from Example 1) was added to a room temperature solution of 30.0 mg of bovine serum albumin (BSA) dissolved in 1.0 ml of PH 9.0, 0.1M sodium borate. The reaction mixture turned cloudy and the pH of the solution was checked using pH paper. The pH of the solution had dropped below 8.5 and small amounts (5 ul-portions) of 2.5% NaOH were spiked into the mixture until a pH of between 8.5-9.0 was reached. After attaining the proper pH, the reaction mixture was stirred for two hours during which time the reaction mixture became clear. Upon completion of the mixing period, the solution was loaded on a Sephadex ® G-25 superfine sizing column (1.5×45 cm) and eluted with pH 7.4 PBS (phosphate balanced saline—10 mM phosphate 150 mM NaCl with 0.05% sodium azide). The benzoylecgonine-BSA was collected as the first peak (as evidenced by a uv monitor) eluted from the column. The benzoylecgonine-BSA solution was concentrated to 9.5 mg/ml (3.2 ml) using a diaflow system equipped with membrane which had a molecular weight cut off of 10,000.

EXAMPLE 3

Benzoylecgonine-bIgG

An unpurified 0.26 ml aliquot of the maleimide derivatized (4-aminomethyl) benzoylecgonine (from Example 1) was added to a room temperature solution of 15.0 mg of bovine gamma-globulin (bIgG) dissolved in 1.0 ml of PH 9.0, 0.1M sodium borate. This reaction mixture was treated in the same manner as the reaction mixture from Example 2. After purification and concentration the final yield was 7.0 ml at 1.75 mg/ml.

EXAMPLE 4

Spotting Tests of Benzoylecgonine-BSA and Benzoylecgonine-bIgG on Nitrocellulose Strips Nitrocellulose membrane was cut into 3×70 mm strips. Four nitrocellulose strips were individually dotted; one with 1 ul of diluted bezoylecgonine-BSA (0.95 mg/ml in PBS), one with benzoylecgonine-bIgG (0.85 mg/ml in PBS), one with a control solution of BSA (1.0 mg/ml in PBS) and one with a control solution bIgG (1.0 mg/ml in PBS). Each of these strips were dipped into a mixture of 10.0 ul anti-benzoylecgonine selenium conjugate and 10.0 ul developing buffer (2% Casein in 0.1% Tween/PBS). The anti-benzoylecgonine selenium conjugate used for this example comprised a monoclonal anti-benzoylecgonine antibody conjugated, by methods well known in the art, to selenium colloid particles. The results of the dipping experiment showed that the strips dotted with benzoylecgonine-BSA and benzoylecgonine-bIgG lit-up at the dotting area as rusty red spots while the two control strips did not.

I claim:

1. A method of coupling compounds comprising the steps of:
   a) forming a maleimide derivative by reacting a maleimide containing compound having the formula:

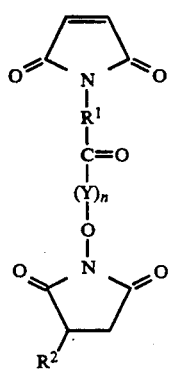

wherein
   $R^1$ is selected from the group consisting of $C_1$–$C_6$ alkyl, benzyl, $C_5$–$C_6$ cycloalkyl and combinations thereof;
   Y is the residue of a substituted or unsubstituted amino acid;
   n is from zero to ten; and
   $R^2$ is selected from the group consisting of H, $KSO_3$, $LiSO_3$ and $NaSO_3$;
   with an amine functional compound capable of displacing the N-hydroxysuccinimide group at a pH of between about 6.0 and 8.0; and
   b) reacting the derivitized maleimide of step (a) with a second amine functional compound at a pH greater than or equal to 8.5.

2. The method of claim 1 wherein said amine functional compounds are selected from the group consisting of primary amines, secondary amines and —$CONHNH_2$ functional compounds.

3. The method of claim 1 wherein said maleimide containing compound is selected from the group consisting of

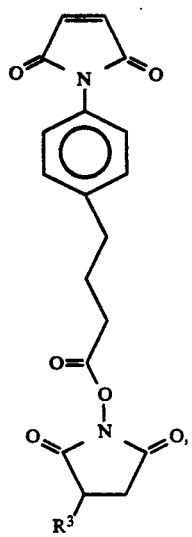

a)

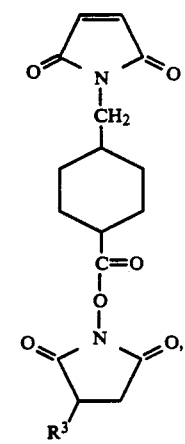

b)

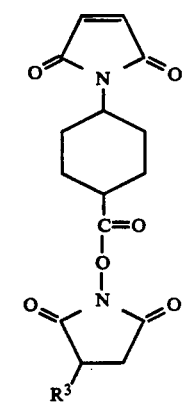

c)

and

-continued

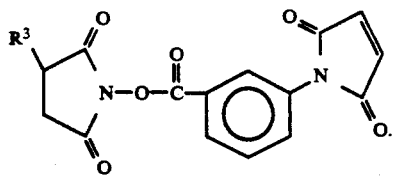

4. The method of claim 1 wherein said pH range for step b) is between about 8.5 and 9.0.

5. The method of claim 1 wherein said amine functional compound of step a) has a molecular weight under 10,000.

6. The method of claim 1 wherein said amine functional compound of step b) has a molecular weight over 10,000.

7. The method of claim 1 wherein said amine functional compound of step a) has a molecular weight less than said amime functional compound of step b).

8. The method of claim 1 wherein said amine functional compound of step a) is (4-aminomethyl)benzoylecgonine hydrochloride and said amine functional compound of step b) is bovine serum albumin.

* * * * *

UNITED STATES PATENT AND TRADEMARK OFFICE
CERTIFICATE OF CORRECTION

PATENT NO. : 5,283,344
DATED : February 1, 1994
INVENTOR(S) : Chi-Deu Chang

It is certified that error appears in the above-indentified patent and that said Letters Patent is hereby corrected as shown below:

Column 6, line 9, change "4-maleimidomethyl)" to -- 4-(N-maleimidomethyl) --.

Signed and Sealed this

Seventeenth Day of October, 1995

Attest:

BRUCE LEHMAN

Attesting Officer

Commissioner of Patents and Trademarks